United States Patent
McIntosh et al.

(10) Patent No.: US 10,475,141 B2
(45) Date of Patent: *Nov. 12, 2019

(54) SYSTEM AND METHOD FOR ADAPTIVE INDIRECT MONITORING OF SUBJECT FOR WELL-BEING IN UNATTENDED SETTING

(71) Applicant: EMPOWERYU, INC., Santa Clara, CA (US)

(72) Inventors: Laura Janet McIntosh, Santa Clara, CA (US); Jeffrey Mark Sieracki, Silver Spring, MD (US)

(73) Assignee: Empoweryu, Inc., Santa Clara, CA (US)

( * ) Notice: Subject to any disclaimer, the term of this patent is extended or adjusted under 35 U.S.C. 154(b) by 491 days.

This patent is subject to a terminal disclaimer.

(21) Appl. No.: 14/616,459

(22) Filed: Feb. 6, 2015

(65) Prior Publication Data
US 2016/0026354 A1     Jan. 28, 2016

Related U.S. Application Data

(60) Provisional application No. 61/936,575, filed on Feb. 6, 2014.

(51) Int. Cl.
*G06N 5/04* (2006.01)
*G06Q 50/22* (2018.01)
*G06Q 10/06* (2012.01)

(52) U.S. Cl.
CPC .............. *G06Q 50/22* (2013.01); *G06Q 10/06* (2013.01)

(58) Field of Classification Search
CPC ....... G06Q 50/22; G06Q 10/06; G06F 3/0484; G06N 99/005; G06N 5/025; G06N 7/005; G06K 9/6256; G06K 9/6269
See application file for complete search history.

(56) References Cited

U.S. PATENT DOCUMENTS

| | | | |
|---|---|---|---|
| 5,751,214 A | 5/1998 | Crowley et al. | |
| 6,540,674 B2 | 4/2003 | Zadrozny et al. | |
| 6,614,348 B2 | 9/2003 | Ciccolo et al. | |
| 6,821,258 B2 | 11/2004 | Reed et al. | |
| 6,950,017 B2 | 9/2005 | Smith | |

(Continued)

*Primary Examiner* — Kakali Chaki
*Assistant Examiner* — Ababacar Seck
(74) *Attorney, Agent, or Firm* — Rosenberg, Klein & Lee

(57) ABSTRACT

A system is provided for event-based monitoring of a subject's well-being within an unattended setting. A plurality of sensors are disposed within the setting for sensing disparate events, and an analytics processing portion is coupled to the sensors to collectively acquire sensing data therefrom, and map a plurality of sensed data points for a selected combination of disparate events to a conduct adaptively characterized for the subject. The mapping occurs according to a set of pre-established reference event patterns, relative to which each characterized conduct is screened for excessive aberration. The analytics processing portion actuates generation of a graphic user interface displaying at least one reporting page. The reporting page contains for each characterized conduct certain graphic indicia determined responsive to the screening thereof. At least one wirelessly coupled monitoring device actuates responsive to the analytics processing portion to render the graphic user interface for a remotely monitoring user.

17 Claims, 9 Drawing Sheets

(56) References Cited

U.S. PATENT DOCUMENTS

| | | |
|---|---|---|
| 6,989,742 B2 | 1/2006 | Ueno et al. |
| 7,113,090 B1 | 9/2006 | Saylor et al. |
| 7,145,461 B2 | 12/2006 | Lehrman et al. |
| 7,188,151 B2 | 3/2007 | Kumar et al. |
| 7,369,680 B2 | 5/2008 | Trajkovic et al. |
| 7,552,030 B2 | 6/2009 | Guralnik et al. |
| 7,589,637 B2 | 9/2009 | Bischoff et al. |
| 8,164,444 B2 | 4/2012 | Anderson et al. |
| 8,164,461 B2 | 4/2012 | Bischoff |
| 8,454,507 B2 | 6/2013 | Tremper et al. |
| 8,682,952 B2 | 3/2014 | Kutzik et al. |
| 2003/0096590 A1 | 5/2003 | Satoh |
| 2005/0137465 A1 | 6/2005 | Cuddihy et al. |
| 2005/0234310 A1 | 10/2005 | Alwan et al. |
| 2009/0322540 A1 | 12/2009 | Richardson et al. |
| 2010/0223071 A1 | 9/2010 | Kland et al. |
| 2011/0173323 A1 | 7/2011 | Fimbel et al. |
| 2013/0095459 A1* | 4/2013 | Tran ................... A61B 5/6816 434/247 |
| 2014/0074504 A1 | 3/2014 | Nelson et al. |
| 2014/0257047 A1* | 9/2014 | Sillay ....................... A61B 5/11 600/301 |
| 2014/0279740 A1 | 9/2014 | Wernevi et al. |

\* cited by examiner

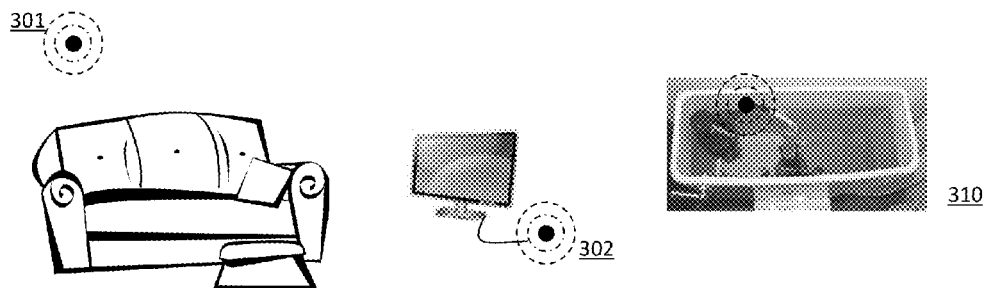
FIG. 3(A)
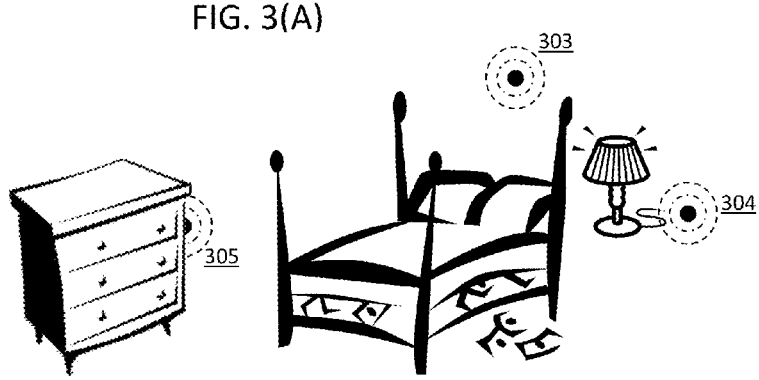
FIG. 3(B)
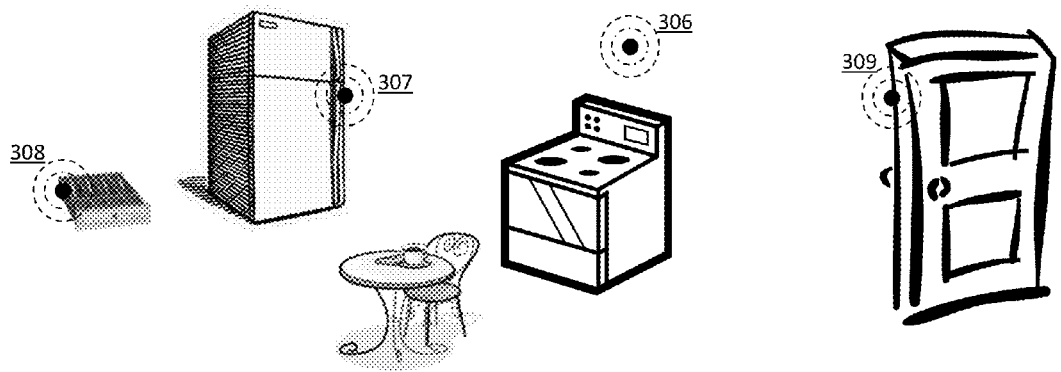
FIG. 3(C)
FIG. 3(D)

SYSTEM AND METHOD FOR ADAPTIVE INDIRECT MONITORING OF SUBJECT FOR WELL-BEING IN UNATTENDED SETTING

RELATED APPLICATION DATA

This Application is based on Provisional Patent Application No. 61/936,575, filed 6 Feb. 2014.

BACKGROUND OF THE INVENTION

The present invention is generally directed to the field of detection and monitoring of a subject's living activities. More specifically, it is directed to a system and method for indirect yet adaptive monitoring of an individual or other living subject's well-being within a predefined setting. The system and method in various embodiments provide for the adaptive monitoring for anomalous conduct within the predefined setting sufficient to raise concerns of the subject's well-being. In certain applications, for example, the system and method provide for the remote autonomous monitoring of an elderly, disabled, or otherwise infirm subject within their usual dwelling place to alert another when sufficiently anomalous conduct is detected. The system and method provide for such monitoring in a discreet and minimally intrusive but highly effective manner.

One's home is a place of comfort, independence, familiarity, and happy memories, and an increasing number of people choose to remain in their own homes for as long as possible, despite increasing infirmities as they get older. However, the elderly are especially vulnerable to falls or sudden illness, and families worry about the safety of loved ones alone at their homes. Attempting to address these issues, some families employ a professional caregiver; but this tends to be expensive and is only reassuring for the time the caregiver is at the home. Communication technologies, such as phones and emergency buttons and similar devices known in the art tend to be effective only so long as an elder is physically willing and able to reach out for help. Legacy security technologies, like video surveillance cameras, are often seen as very intrusive by elders. Moreover, wearable sensors and personal emergency buttons are effective only to the extent the aging adults actively cooperate by actually carry them at all times. Many elders are either unable to consistently remember, or are not entirely willing to carry such personal sensors.

In a similar vein, families or caregivers may wish to similarly monitor the well-being of individuals who may not necessarily be of advanced age, but have physical or mental disabilities. Others may wish to monitor those who may be able to function independently in many degrees but for various other reasons may have limited ability to call for help or report problems during unusual or unexpected situations. Still, some families may be interested in monitoring the status of young-adult children or other individuals who are of lawful age to be left unattended in the family home, but may actually lack the maturity to reliably and responsibly respond to potential situations that may arise.

Systems known in the art have generally provided for highly invasive systems, such as surveillance cameras, which are often unacceptable to one or the other party involved in the monitoring process due to privacy issues. Other systems known in the art have exploited sensors, but report excessive volumes of detailed information to be of practical use to a monitoring user. Too much information similarly tends to create privacy issues, for example by showing a subject's exact location in the house, or reporting their bathroom or other intimately personal habits. Too much information also tends to create information overload for the monitoring user—leaving the end user to sift through, for example, overly detailed movement graphs or sensor triptime information in order to make sense of what conduct the subject person is actually engaged in.

There is therefore need for a system and method which provide for effective yet discreet, minimally intrusive monitoring of a subject's well-being within a certain setting. There is a need for such system and method which offers simple, manageable presentation of information to the monitoring user(s), especially when anomalous conduct is detected.

SUMMARY OF THE INVENTION

It is an object of the present invention to provide a system and method which provide for effective yet discreet, minimally intrusive monitoring of a subject's well-being within a certain setting.

It is another object of the present invention to provide a system and method which provide for indirect monitoring of a subject for anomalous conduct within a predefined setting.

It is yet another object of the present invention to provide a system and method which provide for simple, manageable presentation of information to one or more monitoring users when anomalous conduct is detected.

These and other objects are attained in a system formed in accordance with certain embodiments of the present invention for indirect event-based monitoring of a subject for well-being within a predefined unattended setting. The system generally includes a plurality of sensors disposed within the predefined setting for respectively sensing disparate events occurring therein, and an analytics processing portion coupled to the sensors. The analytics processing portion is programmably configured for execution to collectively acquire sensing data for the disparate events respectively from the sensors, and map a plurality of sensed data points from the acquired sensing data corresponding to a selected combination of the disparate events on to at least one conduct adaptively characterized for the subject. The sensed data points are mapped according to a set of pre-established reference event patterns. The analytics processing portion also executes to screen each characterized conduct for excessive aberration with reference to the pre-established reference event patterns, and to actuate generation of a graphic user interface displaying at least one reporting page. The reporting page contains for each characterized conduct certain graphic indicia determined responsive to the screening thereof. At least one monitoring device is coupled to the analytics processing portion by a wireless communications link. The monitoring device is actuated responsive to the analytics processing portion to render the graphic user interface for a remotely disposed monitoring user.

In accordance with certain embodiments and applications, a system is provided for indirect event-based monitoring of an infirm subject for well-being within a predefined unattended setting. The system generally includes a plurality of sensors disposed within the predefined setting for respectively sensing disparate events occurring within the predefined setting, and an analytics processing portion coupled to the sensors, which analytics processing portion is programmably configured for execution to collectively acquire sensing data for the disparate events respectively from the sensors. The analytics processing portion executes to periodically map a plurality of sensed data points from the acquired sensing data corresponding to a selected combination of the disparate events to at least one conduct adaptively characterized for the subject. The sensed data points are mapped according to a set of pre-established reference event patterns, the acquired sensing data being reduced by the mapping. The analytics processing portion also executes to determine a degree of anomaly for each characterized conduct with respect to the pre-established reference event patterns therein, and to actuate generation of a graphic user interface displaying at least one reporting page that presents a collective summary of the acquired sensing data relating to each conduct characterized for the subject. The reporting page contains for each characterized conduct graphic indicia corresponding to the degree of anomaly determined therefor. At least one remote monitoring device is coupled to the analytics processing portion by a wireless communications link, the monitoring device being actuated responsive to the analytics processing portion to visually render the graphic user interface for a remotely disposed monitoring user.

In accordance with certain other embodiments and applications, a method provides for indirect event-based monitoring of a subject for well-being within a predefined unattended setting. The method generally includes selectively installing a plurality of sensors within the predefined setting to respectively sense disparate events occurring within the predefined setting responsive to daily activity of the subject. A programmably configured analytics processing portion coupled to the sensors is executed to collectively acquire sensing data for the disparate events respectively from the sensors, and to map a plurality of sensed data points from the acquired sensing data, which corresponding to a selected combination of the disparate events, to at least one conduct adaptively characterized for the subject. The sensed data points are mapped according to a set of pre-established reference event patterns. The analytics processing portion is also executed to screen each characterized conduct for excessive aberration with reference to the pre-established reference event patterns, and to actuate generation of a graphic user interface displaying at least one reporting page. The reporting page contains for each characterized conduct certain graphic indicia determined responsive to the screening thereof. At least one monitoring device is coupled to the analytics processing portion by a wireless communications link, and actuated responsive to the analytics processing portion to visually render the graphic user interface for a remotely disposed monitoring user.

BRIEF DESCRIPTION OF THE DRAWINGS

FIGS. 3(A), 3(B), 3(C), and 3(D) are schematic diagrams illustrating various examples of sensor and living space relationships that may be employed to generate a sensor data stream during operation of the embodiment of FIG. 1;

DETAILED DESCRIPTION OF THE PREFERRED EMBODIMENTS

Figure 1:
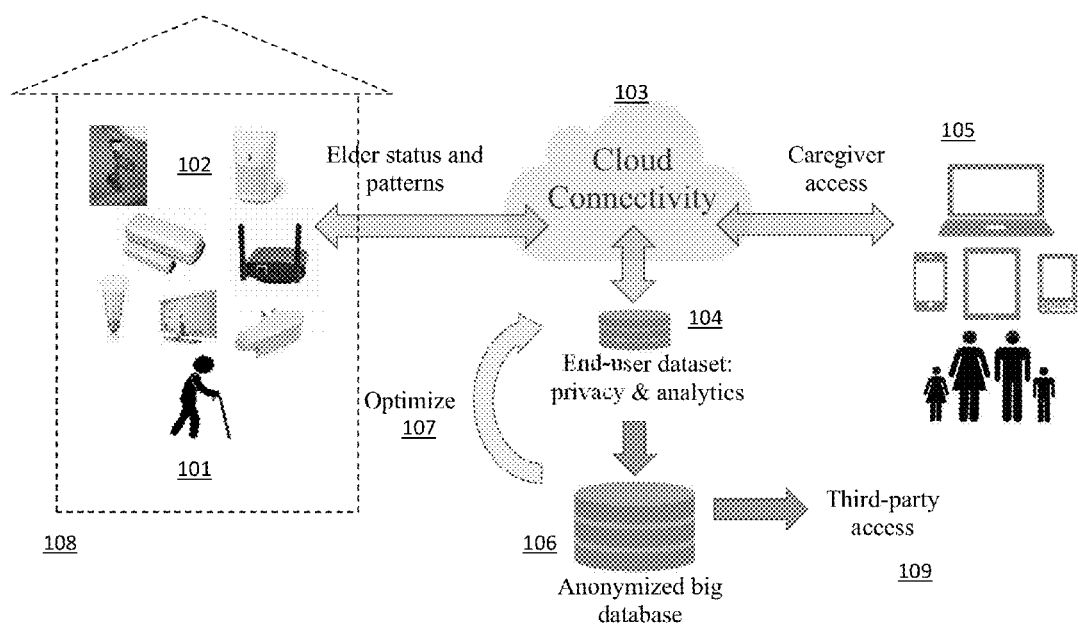
FIG. 1 is schematic diagram illustrating data flow connectivity in a system and/or method formed in accordance with one exemplary embodiment of the present invention.

Generally, a system and method formed in accordance with certain exemplary embodiments of the present invention serves to provide indirect, event-based monitoring of a subject within a predefined setting for anomalous conduct indicating potential disturbance to the subject's well-being. A system implemented in certain embodiments and applications preferably provide for the autonomous logging and summary reporting of specific activities of subject individuals in a controlled environment. The system monitors such individuals such as elders, disabled persons, medical patients, or children circumstantially left unattended for extended periods in a household dwelling place or other predefined setting. The system employs a plurality of various commodity sensors suitably disposed and installed in the given setting, to be available as needed to acquire and provide a data stream helpful to answering key questions of interest to a monitoring third party user, questions relating to the continued well-being of the unattended individual.

The system is preferably configured to provide automated reduction of the sensor-provided data streams to status-indicative elements from which the needed answers may be reliably determined in automated manner. In this regard, the system carries out suitable analytic processing on acquired sensor data to adaptively determine baseline conditions relating to the subject's activity within the predefined setting during particular time periods. Upon selective reduction of the processed data to manageable form, the system delivers the resulting information to one or more monitoring users and presents the same in clearly and succinctly summarized graphic display form. A monitoring user is thereby alerted in a clear, reliable way when a potential threat to the monitored individual's well-being is determined based on detection of sufficiently anomalous conduct at the monitored setting.

In accordance with certain aspects of the present invention, the system preferably reduces the level of data detail exposed to any monitoring user, such that sufficient data detail is provided to indicate whether the subject is safe without exceeding a level of detail comfortable to the subject. This is an important compromise not achieved in monitoring systems known in the art. Additionally, the system preferably reduces the clutter of data to summary conditions that may be easily understood and acted upon by even a non-technical monitoring user. The system thus provides for "at-a-glance" status update displays, preferably employing a graphical user interface that quickly and simply identifies the monitored subject and/or the subject's status of conduct making creative use of non-text visual representations. The system provides an ideal solution for family members seeking daily reassurance that an elderly loved one or other individual residing alone at a remote dwelling is well, and does so non-intrusively, without requiring the monitored person to remember any cooperative action or to necessarily do anything to facilitate monitoring data collection.

As implemented in certain exemplary embodiments, the subject system and method offer an innovative approach that facilitates aging in place, while reassuring family members that their elderly relatives are safe and well while enjoying an independent lifestyle. The implemented system unobtrusively monitors activity inside the subject's dwelling, and the family member or other caregiving individual may at a glance on a Smartphone, tablet, or computer be reassured in the following ways:

1. Notifications—the system preferably generates and delivers suitable notices to them when important daily events for the monitored subject occur, such as the first activity of the day (for example, 'Grandma got out of bed'), or the refrigerator being opened (for example, 'Grandpa is eating at his usual mealtime'), or the like. Notifications may also be sent out when activities occur which are not within an expected, typical pattern, such as activity occurring during the middle of the night and activity occurring at a time when the subject is expected to be away from the monitored premises, among others. The notification parameters may be selectively set by the elder subject, by the elder's monitoring caregiver/representative, or by the system itself according to a default setting.

2. Predictive Analytics—the system preferably creates an activity pattern from the acquired sensor data, then alerts the monitoring user(s) if an expected activity fails to occur as expected (for example, 'Grandpa didn't watch the morning TV news as he normally does—perhaps he should be checked on;' 'Grandma didn't start dinner in the kitchen at the usual time—perhaps she should be checked on').

3. Activity Log—the system preferably establishes and maintains a baseline of activity that may be used as a comparative reference, in order to proactively detect for instance upward or downward behavior trends. The baseline reference may also be used to compare the monitored status pre- and post-event for a certain event or intervention, in order to explain a difference from a prior pattern or to determine a timeline slope from or toward a prior pattern of activity. Examples include a baseline frequency of nighttime waking and trips to the bathroom before and after administration of a pharmaceutical product, or daytime activity before and after introduction of an exercise bicycle or nutrition regimen. The baseline is preferably determined in adaptive manner from an activity log which correlates data from multiple sensors, such as periodic data from an exercise bicycle and periodic data from a weight scale, with measurement data for total daily activity and kitchen activity within the monitored setting/site. The system preferably allows entry of relevant data for purposes of correlation with patterns of activity to aid future predictability—such as, for instance, date of diagnosis of a urinary tract infection entered in order to correlate with frequency of toilet use prior to the date of diagnosis.

In certain preferred embodiments and applications, the system further focuses on logging ordinary daily activates generally experienced by most human subjects in their normal course, such as logging sleep and wake times, meal times, TV or media device use times, arrival and departure times, and general patterns of household activity.

The system in the illustrated embodiment includes a set of sensors strategically-placed throughout the predefined setting, a system controller (gateway), adaptive analytics programmably implemented for execution in the system controller, and software to protect data privacy and actuate presentation of information to designated caregivers or other monitoring users. Preferably, system data is classified according to sensitivity/level of privacy. The data may be designated as view only, may be presented as individual data or aggregate data, or may be downloadable into a secured third party system. The gateway constitutes a robust, compact hub that collects data from sensors, encrypts the information for privacy protection, and sends it to a secure server preferably though not necessarily in the so-called Cloud for storage and for pattern analysis. The system is suitably configured and equipped to provide privacy by design, including measures for meeting data protection standards used by third party oversight and certification standards groups.

The system in the illustrated embodiment is preferably configured to accordingly provide three types of selectable insights:

1. Daily Activities—Families and other monitoring users may choose to be notified by the system when certain specific events occur, such as the first activity of the day.

2. Unusual Events—Alerts are sent if daily activity diverges from prior patterns, which might indicate an accident or illness.

3. Long-term Trends—Trend analysis is carried out to track and characterize changes in activity patterns over time.

The system is preferably customized to individual needs. For example, the system in one embodiment and/or application may require only a few sensors, but users may selectively choose from numerous sensors of various types. Examples include: in home security (e.g. door locks or separation/proximity sensors), energy management (e.g. wireless thermostats or smart plugs), home safety (e.g. smoke alarms and water detectors or flow sensors), health and fitness (e.g. weight scales or exercise bicycles), entertainment (e.g. TVs and audio systems), work space (e.g. printers or computers), lighting (e.g. lamps or bulbs or switches), home automation (e.g. motion sensors or switches), appliances (e.g. stoves or refrigerators or clothes dryers), audio monitors (e.g. baby monitors or glass break sensors), and the like. The system preferably monitors and controls the selected sensors remotely through the same suitable network service provider for extra value and/or convenience.

Each family member and caregiver interacting with the system as a monitoring user via individual communication devices (such as a smartphone) may easily adjust their device access settings to suit individual preferences. Adjustable settings may include for example: a selectively set value for wait time before notification that an expected event was missed, a group of activities selected as important enough for daily updates, and the like. The system may establish connection with devices that push information or communicate to the monitoring user(s) responsive to certain detected events or certain combined strings of events. For example, lack of kitchen activity detection combined with concurrent cooking surface (stove) activation may be sufficiently anomalous to automatically trigger a telephone call to the elder subject being monitored, or otherwise trigger an automated stove turn off control feature that also reports the same to the elder.

The illustrated embodiment is easy to use and may be installed at the subject's dwelling place or other site to be monitored simply by connecting the gateway to an internet router, cellular connection, or any other communications network portal of suitable type known in the art available there at the site. The system's sensors are strategically placed throughout the site so that they may detect typical daily activities directly (i.e. motion sensors) or indirectly (i.e. water flow in a pipe to indicate bathing, toilet, or cooking activities). The sensors are thus placed and installed for operation, so that suitable combinations of their acquired data may be processed to infer in event-based manner the nature of conduct engaged in by the subject. In this way, any conduct of the subject that may be anomalous under prevailing conditions during certain periods/points in time is indirectly detected, so that the monitoring user(s) may be alerted and updated accordingly.

System interaction with a monitoring user is designed for security and simplicity, and to quickly and directly answer the important questions as to the subject's well-being invariably arising in the user's mind rather than providing a sea of data. Preferably, an initial, or login, page presented on a monitoring user's display operably interconnected to the system serves to show at a glance, whether the subject—often a loved one, like a Grandma, is first of all awake and active. Then, responsive to the monitoring user's selected input, more detailed update information is made available for presentation on supporting supplemental display pages.

An additional feature preferably maintained by the system in the illustrated embodiment is an activity log of the type described in preceding paragraphs, which allows a monitoring user to see how certain previous events and intervention actions may have affected the monitored subject's activity pattern. (For example, information as to whether available use of an exercise bike has increased the subject's movement around the house; or, information as to whether prescription of a new medication has reduced night-time trips to the bathroom.) The system is suitably configured to execute adaptive analytics for creating and monitoring activity patterns from acquired sensor data and allow monitoring users to compare recent habits of the subject to past behaviors and proactively detect upward or downward activity trends.

Sustained operation of the system provides monitoring users, who are often caring family members of the subject, the daily reassurance they typically need as to the well-being of the subject, often an aging loved one. Toward that end, the system serves to effectively reduce the available sensor data to quick, succinct summaries intrinsically answering certain basic target questions through clear, instantly understood user interface displays. Typical questions in and elder care situation which are readily answered by such displays include for example:

1. Did Grandma get out of bed today?
2. Is Grandpa eating?
3. Is Grandma on her normal schedule?
4. Did Grandpa go to bed at his usual time?
5. Has there been an accident or illness?

Further details are not generally required, nor typically salient. Under many circumstances, the monitoring user simply wants to know that everything is OK and not have to pay further attention. That is, unless an issue arises or a trend analysis is wanted for longitudinal monitoring.

Various other types of questions may be adapted to situations in which other types of individuals, actions, or items are being monitored. For example, answers may be provided by the system instrically to such other questions as:

a. Has the individual reached home?
b. Has the individual left the house unexpectedly?
c. Has the individual opened the door to a stranger?
d. Is the individual in a part of the house he/she do not belong?
e. Has the individual taken his/her medicine on time?
f. Are there more persons in the house than have been authorized?
g. Are persons in the house at unusual times or when the subject is not home?
h. Has the individual opened a cabinet they should not have (e.g. a gun safe, a poison repository, a medicine or alcohol cabinet)?
i. Is a tagged item moved from its expected location (e.g. medication dispenser lifted, gun removed, food or beverage moved)?

Numerous other such questions may be suitably addressed during the course of system operation in certain embodiments, depending on the particular requirements of the intended application. In accordance with certain aspects of the present invention, such questions whose answers may not seem measurable by automated monitoring are in fact ascertained and effectively communicated to a monitoring user. In the case of questions c, for instance, the answer to whether the monitored individual has opened the door to a stranger may be ascertained by detecting anomalous patterns in a pertinent combination of events—perhaps, upon detection of unusual door opening times without exit or entry.

Turning now to FIG. 1, there are schematically illustrated certain critical data flow and connectivity elements as implemented in a system formed in accordance with one exemplary embodiment of the present invention. The system provides for effective indirect event-based monitoring within a predefined setting 108 for anomalous conduct on the part of one or more subjects 101. A subject 101, such as one or more elderly individuals, is monitored via a plurality of sensors 102 placed in their local environment 108. This environment may be any predefined setting, such as for instance the subject's residential household or dwelling place, or any other place of interest like a place of daytime habitation, a medical or social care center, or a work place. The sensors preferably include any suitable device known in the art for transducing a measurable condition to a sensing signal indicative of the measured condition. The sensors are placed in and around the setting to perform passive monitoring of the target individual(s) without requiring their active interaction with the sensing devices or any other part of the disclosed system. Thus, one or more motion or occupancy sensors may be used to for monitor activity within a specific room or area within the setting 108; one or more motion, separation, or vibrations sensors may be used to monitor for actions such as opening a box, cabinet, door, or refrigerator; one or more power-use sensors may be placed on appliances and lights to monitor their usage; one or more audio sensors tuned to detect specific sounds such as spoken language or breakage/impact may be installed; and, so on.

The system in certain alternate embodiments may include sensor devices placed on or about the target person, such as a panic alert button, accelerometer, etc., in accordance with various aspects of the spirit of the invention. These devices however, require active cooperation by the subject to ensure proper acquisition of target status information. Where such devices are employed, it becomes useful to automatically determine the status of the device—e.g., has the user put on their personal monitor or not?—thus, such extraneous information as whether or not the device is personally worn by the subject must be factored into the system analytics.

The monitored environment/setting 108 is linked via suitable communications measures to other portions of the system. The system's processing is preferably located remotely, on a common resource such as cloud connected server for instance; however, in certain embodiments such processing components of the system may operate on a local gateway or other processor within the monitored environment.

The cloud connectivity 103 comprises an interlinked series of communication networks of any suitable type known in the art, including, for example, the internet, mobile service networks, and the like, which jointly facilitate links between the sensing, processing, storage, and reporting portions of the illustratively embodied system.

Figure 2A:
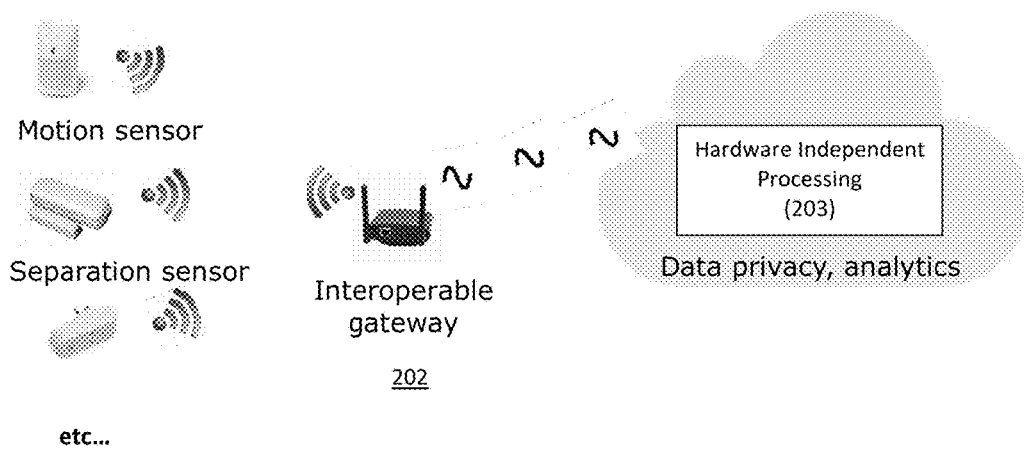
FIGS. 2(A)-2(B) are schematic diagram illustrating operational intercoupling between various examples of sensors collectively available in a dwelling place and a hardware independent processing portion during operation of the embodiment of FIG. 1.
Figure 2B:
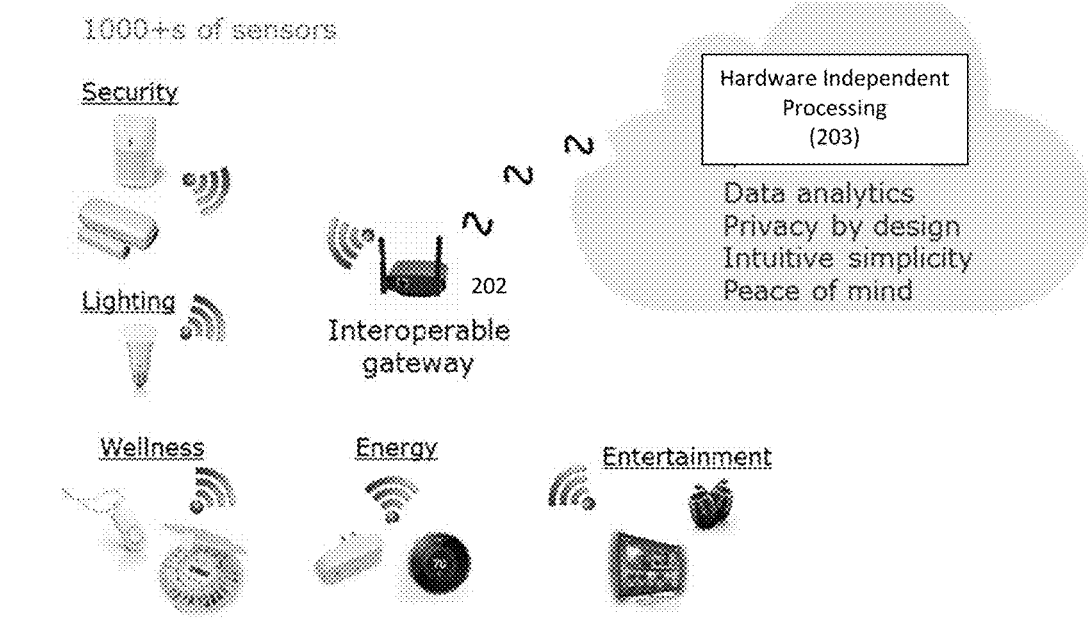

As illustrated in FIG. 2, sensors 201 are typically connected locally to a gateway 202 within the environment of the target user, and this gateway concentrates information and transmits the same via the cloud to a primary processing portion 203. The sensors may be wired or wireless, as needed for the intended application. In one exemplary applications, a collection of z-wave based sensing devices are employed, linked to a gateway, with the gateway transmitting summary information via the internet out of the household environment 108. Sensors in various embodiments may be directly connected via network protocols such as TCP-IP so that the gateway may be replaced by a conventional router device. Thus, smart lights, thermostats, appliances, TV's, etc., may be suitably incorporated into the system's data gathering network in accordance with certain aspects of the present inventions.

The cloud-based primary processing portion 203 is preferably operable independent of the particular hardware which may be employed for sensing and transmission. As such, the primary processing portion is substantially adaptable for use with any available set of sensors or gateways from any vendor without substantial modification.

Referring back to FIG. 1, the system records user sensor data in an end-user specific dataset 104, on which data user-specific analytics are executed by the primary processing portion, as described further below. User privacy is thereby maintained via all communications channels, and such user-specific data is logically isolated so as to prevent propagation of information that might unduly compromise the target individual's privacy.

Putting aside for the moment the measures by which the analytics dataset operates, status information is provided only to monitoring parties having proper permission to receive it. Thus only caregivers, family members, and/or others having authorized relationship to the target individual being monitored may at any time access the target individual's status reports via Smartphone, tablet, website systems, or the like (105). As further described below, sensor data streams from sensors 102 are considerably reduced via suitable analytics to "at-a-glance" understandable status information for the monitoring users at remote devices 105. This provides advances over the art in minimizing the time, technical know-how, and skills necessary to assess the status of the person of interest and reducing dependence on any given monitoring user's personal ability to interpret and assess sensor data on their own.

The system operates to detect anomalies in the monitored subject's conduct within the predefined setting 108 based on events collectively sensed by the various sensors 102. The system then classifies the detected anomalies as those likely to represent harm to the subject individual, and in the event of possible harm, provide timely information to the monitoring users that the target person may require their attention. Some anomalies detected as such may not actually be classified as likely to represent harm where the system recognizes sufficient contextual factors to allay the concern. As described herein with reference to FIG. 9, for example, the system operates in certain embodiments to first classify event TYPES by tokenizing them, and searches within and across each of these TYPES for anomalies the given event pattern. Then, based on the TYPE of behavior and the degree of anomaly, the system in such embodiments determines a THREAT or CONCERN level for classification of detected anomalies. This keeps the system from bringing undue alarm to monitoring users.

For example, by tracking regularity of bed-time activities, the system detects and alerts/reports to the monitoring user when the target subject fails to rise from bed as expected. By tracking patterns of kitchen activity, the system detects and alerts/reports when the target subject misses a meal, or otherwise eats less/more frequently than what had been typical in the past. By tracking patterns of activity about the house, the system detects and alerts/reports when an individual is unusually inactive, potentially signaling need for require help or intervention. By tracking the environment's occupancy and exit/entry information, the system detects and alerts/reports when an individual has left the environment at an inappropriate time, or has failed to return by a typical, expected time. By tracking electrical usage of an appliance such as a TV, the system detects and alerts/reports when a typical viewing time is missed.

The system in certain embodiments, also operates to moderate or otherwise screen reports of increases/decreases or other perceived changes in normal expected activity due to context. For example, an increase in kitchen activity corresponding to a smoke alarm alert might normally trigger the system to detect an anomaly and accordingly report concern to a caregiver, whereas sensing only increased activity in the kitchen and family room may not constitute a sufficiently anomalous conduct and therefore suppress alert.

The precise events of interest, and the level and combination thereof required for anomaly detection and triggering of alert will depend on various prevailing factors for the given subject(s). For example, they may vary according to the household being monitored, the target individual's habits, and certain concerns of the monitoring users. As described further below, the system preferably executes to adaptively learn and determine not only the target individuals' patterns of conduct, but also the expected ranges of variance in their habitual patterns of conduct. This minimizes the likelihood of over-reporting anomalies that would appear as false-alarms from the monitoring users' perspective. This also represents an improvement over known systems in which users define preset fixed schedules (e.g., typical wake up time) and receives notices of missed scheduled events in a non-adaptive fashion.

The monitoring individuals in various embodiments of the system and method disclosed herein are preferably given access selectively—depending on their identity or relationship/function as to the subject, only to some or all of the data stream, or just to a summary of the data. For example, in a typical application of the illustrated embodiment, a family member of an elder subject may be granted selective access to all of the subject's daily activity. On the other hand, a medical caregiver may be granted selective access only have the subject's health-related data, such as records of blood-pressure cuff readings, weight scale readings, or the like.

The system preferably offers monitoring individuals certain report options, like the graphic presentation of summary information in primarily numeric or primarily graphic form, and the inclusion of a time indicia component if desired. Quantified data will be stored and can be presented in absolute value or compared to a calculated baseline.

When an anomaly in conduct is detected by the system, corresponding information is reported to the monitoring user(s), such that the report is available to alert them when the monitoring user(s) next check-in from their devices. In this regard, the system generates and sends a suitable notification signal to each monitoring user according to the settings in its software configuration. Concurrent notice is preferably also sent to each monitoring user via other measures such as: by push notification via phone call, text, email, app. alert, or the like. The system preferably allows each monitoring user to set their threshold of interest in anomalies and their preferred means of notification. In this context, the monitoring user's threshold of interest is preferably interpreted as a threshold or weighting factor on the degree to which a pattern must be anomalous before the monitoring user is notified. For example, in one illustrative embodiment using a normal statistical distribution of event occurrence times, a threshold of interest may be interpreted to trigger notification to the monitoring user whenever an expected event time exceeds a z-scored adjusted distance from the mean occurrence time While maintaining the privacy of the target subject's sensitive data details in the dataset 104, the system in this embodiment also accommodates aggregate analysis of different subjects' datasets. This is achieved by anonymizing each end-user's data, removing personally identifiable information to produce a conglomerate database 106. This provides a number of useful features. For instance, various longitudinal analytics over groups of users may be carried out, thus permitting patterns and behaviors typified over multiple households and situations to be abstracted and fed back to the individual levels of analytics through a suitably configured optimization process 107. In addition, this large database may be mined for behavioral information and other details of interest to third parties 109 engaged in various types of product development, research, or the like.

Returning to certain details of monitoring target subjects, FIGS. 3(A)-3(D) schematically illustrate specific examples of the sources and monitoring points typically found in a residential or other dwelling place of a monitored subject. As noted herein, a common application of the disclosed system is found, for example, in the monitoring of subject individuals for well-being in their home. In keeping with the goals of intrinsically answering specific natural questions on the subject's status and condition, as discussed above, the system preferably monitors a plurality of distinct areas within a given subject's setting. In addition to the examples noted in preceding paragraphs for the sensors that may be employed; similar or additional event-indicating information may be obtained using sensor devices of any suitable type known in the art appropriate for the given setting. Practical considerations like cost and convenience will normally dictate where and how many sensor devices are actually placed and used. A combination of sensors suitable for a particularly intended application are preferably employed to provide as much knowledge/information acquisition as possible while employing as few sensor devices as possible (in as economical a manner as possible). Further, sensor types that do not collect unneeded information are preferably employed, both to minimize invasion of the subject's privacy and to minimized data flow rates.

In FIG. 3(A) illustrates examples of sensors installed to monitor distinct living spaces within the monitored subject's setting 108. A space such as a living room or office is fitted with a motion/occupancy sensor 301 in this example, employing such passive sensing devices of infrared, ultrasonic, RF, or other emissions according to any suitable technology well established in the art. Where used in an occupancy mode, a sensor activated for the system operates to record when activity has occurred in a room or designated living space within a block of time, say 4 minutes for instance. The sensor may also operate to record when a prolonged condition of stillness occurs within the room in a manner not consistent with the ordinary course of activity there—perhaps because of an adverse event such as fall or illness. The system preferably carries out such interpretive operation.

Lack of activity in the room may be mapped to an unoccupied condition. Where used in a motion detection mode, the same sensor may report activity and lack of activity on a much tighter time schedule, say 10-30 seconds for instance, thus providing the analytic processing portion of the system with a finer grain set of information with which to work. This tradeoff is preferably made in practice considering not only the analytic needs of the system, but also the higher energy costs incurred by the more frequent reports being generated and transmitted (such as the potential reduction battery life of sensor devices). In certain embodiments, other areas of the house such as hallways and stairs are monitored with motion detectors to track transitory movement between floors and rooms within the house.

Also illustrated in FIG. 3(A) is a sensor to sense TV watching activity. As shown, a TV connected to the wall power socket is monitored by a power-usage monitor device 302 installed on the power connection. The device 302, which may be of any suitable type known in the art, senses and provides to the system's processing portion the amount of power in use at any given time, thus allowing the system to track those periods when the TV is turned on. The system may thus track the subject's regular habit of watching TV programs, for example, and establish patterns within this feature set for later comparison and anomaly testing. A subject's failure to follow a habitually established watching schedule, or the subject's failure to exhibit any watching activity at all during expected time periods may form one basis for alerting the monitoring user(s).

Such a sensor is preferably connected to a power consuming appliance or other equipment/device known to be used regularly by the target subject within the monitored setting. Other examples may include in addition to a TV: a coffee maker or toaster, a radio, a room/area illumination lamp, a reading lamp, a microwave oven, etc. The selection of device is ideally made to suit each system application based on certain prior knowledge of the target subject's habits. This instrumentation of selected appliances, equipment, devices within a subject's monitored setting, and configuration of the system's analytics to adaptively determine which appliances/equipment/devices deliver the most salient activity patterns are features that may be utilized in certain embodiments, depending on the particular tendencies of the subject and nature of the monitored setting.

FIG. 3(B) schematically illustrates sensor placement in a bedroom for certain embodiments of the system. A motion/occupancy sensor 303 is preferably employed and positioned on a wall or ceiling surface with its field of view oriented to encompass much if not all of the space at and around the bed in the room. The sensor's data stream would provide information as to when an individual has gotten out of bed or is moving around the bedroom. Once such activity ceases, and is followed by no other activity elsewhere in the house for a period thereafter, the system may, for example, infer that the target individual has gone to bed. Preferably, this detection is augmented by tracking a subject's estimated current state against a hypothesized change in state. In one particular example, once an individual falls into a verified sleep state, events within the bedroom (such as rolling around in bed) are down weighted against events that occur outside the bedroom so that spurious wake-up times are not erroneously generated. Such bedroom-related events are tracked according to their regularity, and statistical inferences of the likelihood of a subject having gone to bed in the normal course of a particular day may be drawn based on pertinent factors. For example, the anomaly of this activity pattern may be weighed in view of the time during the given day at which it occurs.

Also illustrated in FIG. 3(B) is a power-use monitoring sensor of any suitable type known in the art coupled to a bedside lamp 304. This sensor enables the system to track when the target subject is using the lamp 304, or conversely when the subject has turned the lamp off for sleep or rest. It will be clear that other sensing measures, including light metering, smart-light bulbs, pressure sensors, audio monitors, or the like known in the art may be employed as well to acquire equivalent data. The coupling or substantial concurrency of events such as bedroom activity, followed by a lamp being used and then turned out, may represent a typical pattern for certain subjects, indicating their turning in for the night. Joint, even redundant, information provided by multiple convergent data points tends to heighten confidence in the system's reliable estimation of the subject individual's activity status, hence the system's reliable indication of the subject individual's well-being. In particular, joint detection of occurrences which are separately irregular enough to cause concern heighten confidence all the more of anomalous activity, and the system accordingly forwards the same to each monitoring user through alert notices for review. Sensor data integration in this regard provides synergistic advantages over simply detecting and reporting disparate sensor activity.

Other supporting instrumentation for bedroom monitoring may include, for example, one or more separation sensors 305 attached to dresser drawers. Various other sensors like an accelerometer or a light sensor may be alternatively employed to provide equivalent information. The dresser drawer is but one example of equipment whose use/activation may be monitored in this regard. Other examples of equipment which may provide strategic sensing points include but are not limited to bathroom doors, closets doors, medicine cabinets, pill boxes, or glasses, watches, and other typical daily adornments, among others.

Bathroom monitoring in certain embodiments may include, for example, motion sensors as well as water use monitors attached to pipes in the sink and/or toilet (310), or audio monitors capable of detecting sounds indicative of a fall or consistent with language of distress. Humidity and water sensors may also be placed to detect normal washing events. Sensors may be employed as well to detect potential hazards—examples including sensors to sense water spillage that may indicate unsafe slippery floor conditions or leakage/overflow due to damaged plumbing. Health and fitness monitoring devices may be employed to provide both a data stream and a time context for determining proper activity and medication regimens.

Typical areas of particular interest within a subject's dwelling in the illustrated embodiment are the kitchen and eating areas. As illustrated in FIG. 3(C), one or more motion/occupancy sensors 306 may be employed to monitor such kitchen and eating areas. In addition, sensors 306 for heat may be employed near a stove, and sensors pertaining to light may be employed elsewhere to determine when lighting for the room or area is in use. These sensors sense nominal levels to help the system establish a baseline, so that when aberrant levels are sensed, or when otherwise normal sensed levels collectively exhibit aberrant patterns, anomalous activity may be discerned.

Also illustrated in FIG. 3(C) is a sensor 307 installed to determine when a refrigerator door is opened. Note in this regard that certain modern appliances, including refrigerators, stoves, and others known in the art for the kitchen and elsewhere, now provide integrated smart network enabled technology that may obviate the need for any extraneous sensor to sense door opening or other operating conditions. Where such smart appliances are employed and linked to the system, the system may communicate directly with the device through its built-in operational monitoring and communications interface capabilities to acquire its activity status. FIG. 3(C) also illustrates sensor instrumentation provided for a utensil drawer, the opening/closing activity of which is often associated with food preparation or, more directly, with eating. These are but some examples of the numerous sensor provisions that may be made in the illustrated system.

Other examples in the kitchen context include sensing capabilities incorporated with pantry or cabinet doors, and the like. Instrumentation for various other types of devices such as water, heat, carbon monoxide, and smoke sensors may also be placed in the kitchen context to monitor activity and safety. Particularly within the kitchen, multiple types of sensors are preferably employed not only to acquire information also to trigger immediate automated actions on the premises. A sensed lack of activity for a certain extended period coupled incongruently with elevated temperature or ongoing energy use of stove, for instance, might prompt the system to trigger a 'burner off' automated command mechanism to shut the stove off and/or notify a designated caregiver. Such other incongruent conditions as low temperatures and differentials between the kitchen area and other living spaces of the monitored site may also trigger automated actions like notifications, especially where the potential consequences for failure to take prompt remedial action are severe (for example, lack of heat unduly jeopardizing safety in the wintertime).

Based on patterns of sensor information within the food-prep and eating areas, the system preferably determines whether and when a target subject is preparing meals, snacks, and so forth. The system generates a set of reporting displays consistent with the determination whose contents effectively and preemptively answer basic questions that would come to mind for concerned family members, caregivers, or other monitoring users. Answers to questions like whether the subject is eating and whether he/she is doing so regularly and consistently are presented, so that monitoring users may be reassured or alerted accordingly. This provides one of numerous information data points that may be reflected in the system's periodic or as-needed reports and alerts to monitoring users.

As indicated in FIG. 3(D), other distinct areas preferably monitored by the system are doorways. Suitable devices such as contact sensors, for instance, acquire entrance and exit data which, when coupled with other data points indicative of certain activity or lack of that activity, enable reliable determination of the monitored subject's leaving and returning to the monitored environment.

Figure 4:
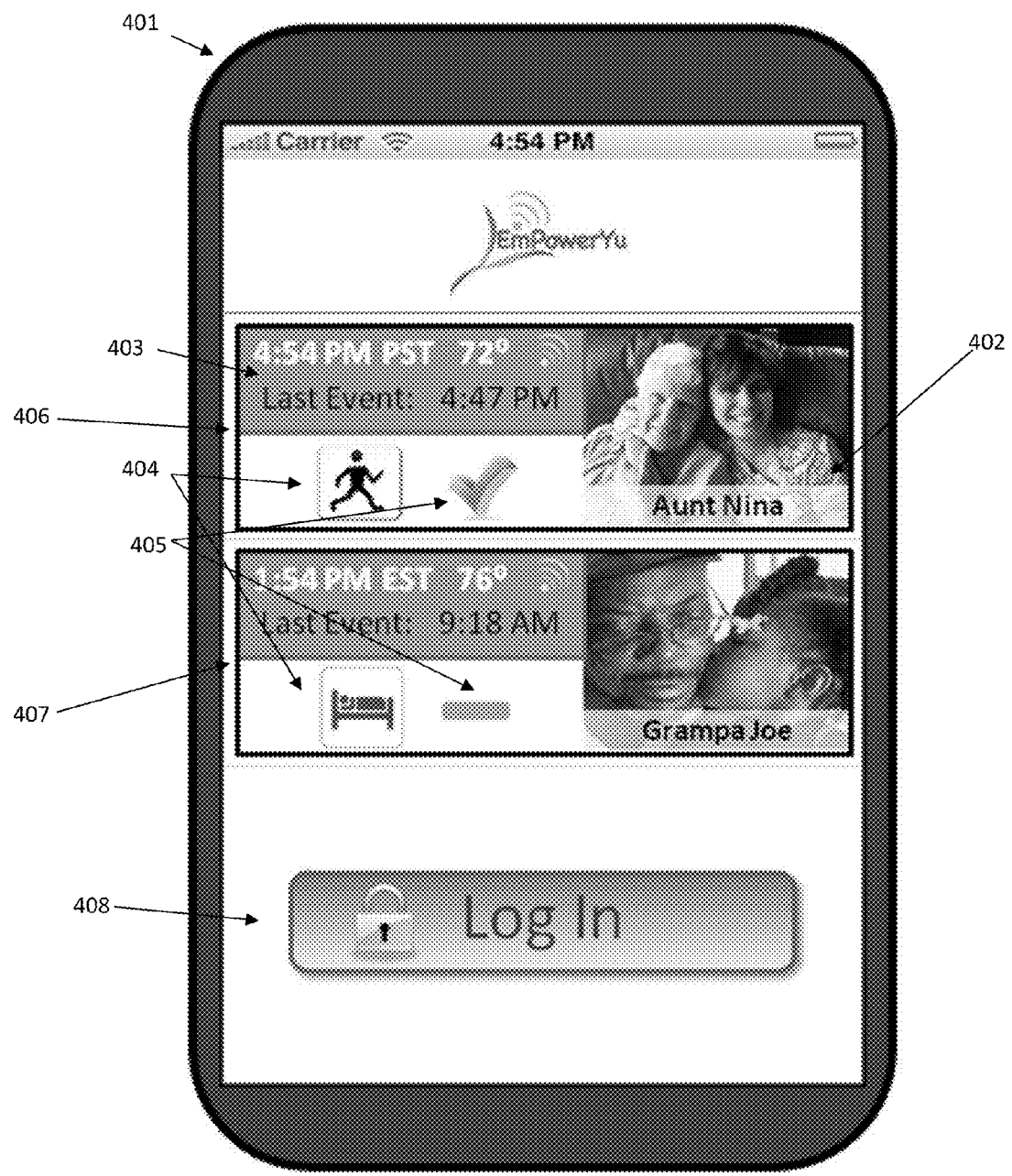
FIG. 4 is an illustrative view showing one example of graphic user interface display established as a mobile log-in page for a monitoring user during operation of the embodiment of FIG. 1, wherein information of various subjects' activity state information are presented in reduced form.

FIG. 4 shows one example of a high level graphic user interface reporting page generated and displayed initially for a monitoring user on his/her system-linked device in one sample application of the illustrated system embodiment. The graphic reporting page generated and displayed by the system reflects a culmination of guiding factors, or goals. One goal is the reduction of data to "at-a-glance" status summaries from which a monitoring user may instantly glean the current overall well-being of the monitored subject. Another goal is to provide simple yet emotionally favorable, attractive, and easily identifiable visual representation(s) of the subject(s). Yet another goal is to provide clean, convenient dissemination of information to monitoring users, preferably through a graphic user interface which reports salient information using minimal textual content.

Figure 5:
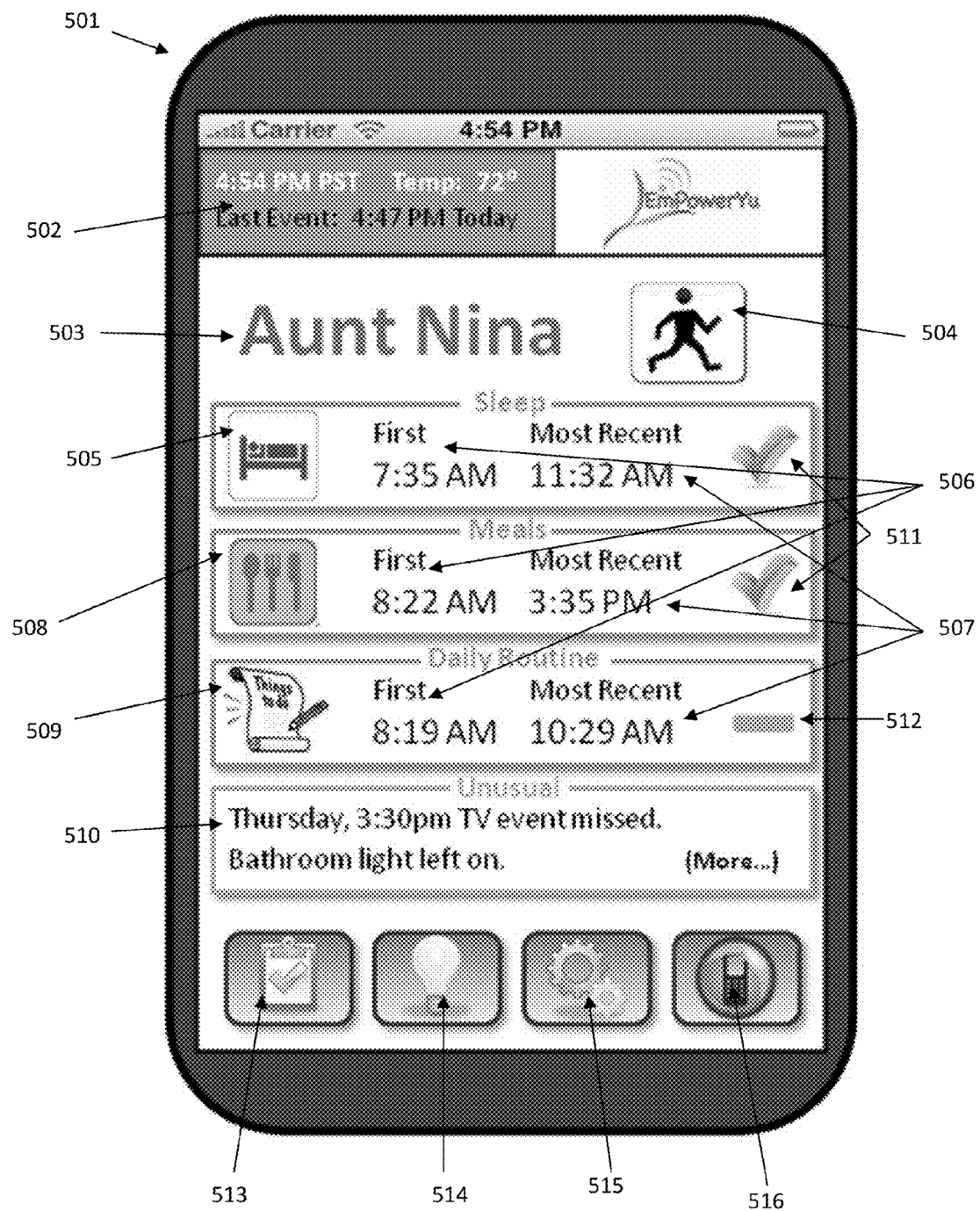
FIG. 5 is an illustrative view showing another example of graphic user interface display established as a more detailed level mobile page for a certain monitoring user relating to the monitoring of one selected subject identified on the page of FIG. 4 during operation of the embodiment of FIG. 1.
Figure 6:
FIG. 6 is an illustrative view showing another example of graphic user interface display established for another monitoring user as a larger screen format display of similar information presented in FIG. 4, but suited for a tablet, lap-top, desktop computer or other such display device, during operation of the embodiment of FIG. 1.

As illustrated, salient information is thus presented to monitoring users through graphic reporting pages which reflect the system's adaptive mapping of various events indicated by acquired data points (via the various sensors) to particular behavioral conduct of the subject. This event-based mapping of events to particular conduct is processed by the system from an inferential synthesis of acquired sensor data having disparate type in view of known or learned data relating to the subject, the subject's health condition and/or particular infirmities, data relating to the monitored setting, time of day, season during the year, and/or other factors applicable to the intended application. Examples of such mappings for the sample scenarios illustratively displayed in graphic reporting pages like those shown in FIGS. 4-6 are addressed below:

Aunt Nina

1. Her wakeup detected by movement in the bedroom and then activity on sensors outside the bedroom occurred at 7:35 AM. She later had a brief morning nap ending at 11:32 AM, as detected in the same fashion. These are within normal limits, therefore a green check is displayed (511) is displayed.

2. Activity in the kitchen including occupancy, refrigerator openings, and utensil drawer openings peaked first at 8:22 AM, thus indicating a first meal (i.e., breakfast). Later meals included, most recently, a tea time snack at 3:35 PM. These all occurred within normal times of day, therefore a green check (511) is displayed.

3. Her daily routine events started with a TV being turned on (sensed by a smart switch) at 8: AM (506), and a set of organizational activities in her living room sere sensed at 10:29 AM. Both of these activities are typical; however, she did not watch her usual 3:30 PM TV show (510), therefore a conspicuously colored (such as orange) bar (512) indicating anomalous activity is displayed.

4. Based on this aggregate information, her current overall state is still normal as shown by green check (405) in FIG. 4. The missed activity in itself is not sufficient to trigger a concerning anomaly since she did complete her expected tea-time snack at or after the same time frame.

5. Otherwise, Aunt Nina is indicated to be up and about (404), with temperature and system connectivity being nominal (403).

Grampa Joe

1. Grampa Joe's detail page is not shown; however, from his summary page in FIG. 4 we it is evident that temperature in his house is normal, and his gateway is connected. But there is a significant anomaly.

2. His last event was at 9:18 AM, and the system has determined by monitoring the pattern of occupancy and stillness that he is now in bed (404) and has been there all day. As it is 1:45 PM in the afternoon, and his ordinary wakeup time is 8:30 AM, the system interprets this as a strong anomaly, as indicated by the colored (orange) bar (405). This suggests that the monitoring user should investigate.

3. In certain preferred embodiments, such a strong anomaly also triggers a push notification to the caregiver so that they are directed to check the GUI details and check on the subject.

In the example of FIG. 4, the high level graphic reporting page also serves as a Login page for a monitoring user. The reporting page is graphically presented to the user through a suitably configured software application, or "app," running on a hand-held smartphone device 401. The reporting page may be alternatively presented on a communication device of numerous other types known in the art, facilitated by other known software interface tools such as through website pages accessed through a suitable internet browser or other known data presentation modality. This initial (high level) user interface display in the illustrated example is divided into different display blocks/frames 406 and 407, which respectively summarize the individual status of two target subjects being separately monitored. In the sample scenario, the subjects are labeled "Aunt Nina" and "Grampa Joe."

To provide instant recognition, each block includes a personalized title and picture in one frame area 402, the picture preferably being uploaded by the monitoring user. Each block further includes a textual summary of pertinent situational status information 403, which include in this example indications of: the local time at each individual subject's monitored setting (dwelling place), the current temperature in their dwelling, and status of the system's operational connectivity (whether the gateway at that dwelling is on-line and actively reporting information), and the time of the last event recognized by the system's analytics portion. Thus the monitoring user knows from a quick glance at the reporting page whether the dwelling is sufficiently comfortable for each subject, whether the monitoring system is in place up and running, and how current the last updated of pertinent information is.

In addition, each display block preferably includes a summary icon 404 that informs the monitoring user at a glance the current status of each individual subject. In the sample scenario, Aunt Nina is reported currently as being active (denoted by a walking stick figure in the subject's icon 404), suggesting that she is up and about the house, while Grampa Joe is reported as still being in bed. These icons 404 represent a state-estimate of each target subject as determined by the system's analytics portion. Other icons that may be employed, including for example: a meal symbol for eating (not shown), an empty-house icon for having left home (not shown), and numerous others suited for the particular application intended.

Another graphic feature employed for enhancing at-a-glance retrieval of information in each display block is preferably a nominal vs. negative (likely of concern) anomalous indication 405. Aunt Nina is reported by virtue of the green check symbol 405 to be following her usual daily event course and therefore without anomalous conduct. But Grampa Joe is reported by virtue of the brightly colored (orange) dash to not be doing so. Thus the monitoring user is informed at a glance which subject is currently OK, and which subject potentially needs to be checked on.

The system in this manner reduces a multiplicity of potentially confusing event sensor streams by collecting then appropriately combining and inferring therefrom, so as to map the same to qualitative estimations of the subject's behavioral activity. The pertinent activities are presented in at-a-glance information summaries, which may be accessed remotely with one tap of an identifying icon on the main smartphone display page for the system. The pertinent activity information is presented in a manner that minimizes intrusion into the privacy of the target subject. This is of particular importance to many elders concerned about their privacy, whose consent to monitoring may be conditioned on adequate assurance in this regard. The system balances the often competing interests of restraining and limiting intrusion into the subject's privacy with those of maintaining meaningful access to concerned caregivers needing fast and easy access to up-to-date information on the subject's well-being. The system preferably enables access to monitoring caregiver(s) with minimum numbers of screens to navigate through, such as by enabling one tap on a system-designated icon to a high level reporting screen for any individuals being monitored by that caregiver.

In the illustrated example, the app shown in FIG. 4 preferably includes a log-in button 408, by which the monitoring user may log into the system to get more information about the status and recent activities of the target subjects that particular user is authorized to monitor. Authorization will in certain embodiments be controlled only by the subject or by his/her duly appointed representative (such as individual granted the subject's power of attorney).

FIG. 5 shows another example of a graphic user interface reporting page generated and displayed for a monitoring user on his/her system-linked device in one sample application of the illustrated system embodiment. As opposed to the reporting page shown in FIG. 4, the reporting page displayed in FIG. 5 is displayed at more detailed level once the monitoring user has actually logged into the system. In this case, an expanded view of the updated activity data is presented for one of the multiple subjects being monitored in this example, "Aunt Nina's," whose selection corresponds to the high level summary presented in display block 406 of FIG. 4. This more detailed access to the given subject's monitored information, which goes beyond the initial alert of any anomalies in the subject's activity, is included in this particular example. In alternate embodiments and/or applications, the system may simply provide a monitoring user access only to the high level summaries of activity pertinent to a given anomaly alert, as illustrated in the initial login page of FIG. 4, recognizing that the alert would invariably prompt a monitoring user to take immediate remedial action, like phoning the subject or otherwise arranging the necessary intervention rather than reviewing further analytics at that point.

In the example shown in FIG. 5, the display block 502 reports ambient data such as time/date/temperature, similar to that reported in display block 403 of FIG. 4. The target subject's name or other identifying designation serves to label the page 503, and the overall status icon 504 is placed clearly and conspicuously (such as near the top) on the page display. The display page is subdivided beneath that into various frames each relating to certain selected categories of interest for the given application. In display block 505, for instance, sleep-related information is graphically denoted and summarized. A graphic icon is preferably displayed in each frame to highlight the type of information to be presented in that frame. Time tags 506, 507 for the First and Most Recent events of the day in the frame's category are reported for quick reference in this example.

Thus, if the system were to determine by virtue of an extended period of inactivity in the bedroom (and elsewhere) followed by activity after 7:35 AM, the system would infer that the subject got out of bed at 7:35 AM, and log the activity as constituting a sleep-related event. If, for example, the system were to determine by virtue of the reverse sequence of events (bedroom activity followed by extended period of inactivity there and elsewhere), the system would infer that the target subject laid down for a rest at the delineating time, or 11:32 AM in this particular example. This too would likewise be logged as a sleep-related event.

Within each framed category, a clear, prominent icon or other indicia 511, 512 is displayed for each frame, so as to communicate nominal (511) vs. anomalous (512) conditions. This helps the monitoring user to quickly recognize—at a glance—whether the target subject is following his/her typical behaviors/conduct for the day in each event category. Also shown in this example are frames for a meals category 508 and a daily routine category 509. The meals category is linked, for instance, to events occurring in the kitchen and eating areas as described above. The daily routine category that encompasses various activities such as the subject's movements about the house, his/her use of appliances like TVs or reading lamps, and passage into and out of the house (entry/exit). The system preferably provides each monitoring user with the option to selectively configure other categories of interest (e.g. bathroom events, occupancy events, etc.) and display their graphic presentation frames as a supplement to or substitute for one or more of the categories shown.

A display block 510 is preferably generated on this reporting page for one or more of the framed categories in which an anomalous event is detected (denoted by indicia 512). The display block 510 is graphically highlighted for visual reference to the indicia 512 for anomaly detection (outlined by a brightly colored border to match the brightly colored dash of indicia 512 in this example). The block 510 displays therein available information pertaining to the anomalous condition(s) from one or more categories. The pertinent information is summarized to aid the monitoring user's quick apprehension of the anomalous situation, such that the monitoring user may learn the nature of the anomaly and immediately determine whether it warrants further action or remedial response. In this example, the details for the detected anomaly indicate a missed TV watching event and that a bathroom light was left on when it is usually turned off.

The monitoring user may access unusual events and indicate whether this category of event should result in a notification; a bathroom light left on may be an anomalous event, but not worthy of notification, whereas a specific missed TV event may be a strong indication of harm that is desirous of notification by the caregiver. System flexibility is given to the caregiver whenever possible to customize the notifications to reflect the caregiver's knowledge of the subject user.

At the bottom of this graphic reporting page are preferably displayed one or more other reporting pages, each selectively represented by respective graphic buttons for access thereto. In this example, button 513 provides selective access to a log of events so that the monitoring user can review in more detail the occurrences on which the analytics processing portion has based its inferences/conclusions. Button 514 provides selective access to instant status reporting of the sensors within the subject's environment so that conditions may be monitored substantially in real-time. Button 515 provides selective access to setup and configuration information. Button 516 provides convenient actuation of the given device's telephone or other designated voice communication resource to verbally contact the target subject him-/herself or another party on the subject's behalf. For example, activating button 516 may in this instance pull up Aunt Nina's phone number and place a phone call to her directly through the given smartphone device.

FIG. 6 illustrates an example of an alternate layout for presenting much the same information presented by the more detailed information reporting page of FIG. 5. In this alternate example, the reporting page is displayed in an extended layout formatted for a larger-screen device. Such extended layout may be suitably configured and employed when a monitoring user checks activity status of the target subjects from a desktop, lap-top, or table computer device, for example. The changes in this extended layout (from the layout shown in FIG. 5) include more textual details in the information category frames. An emergency button is also included in this example, which permits the monitoring user to immediately initiate a call to emergency services should their review of a target subject's activity status warrant such measures. Such an option when present is preferably provided with suitably incorporated safeguards known in the art to protect against accidental activation (for example, by employing one or more layers of activation/command confirmation).

Figure 7:
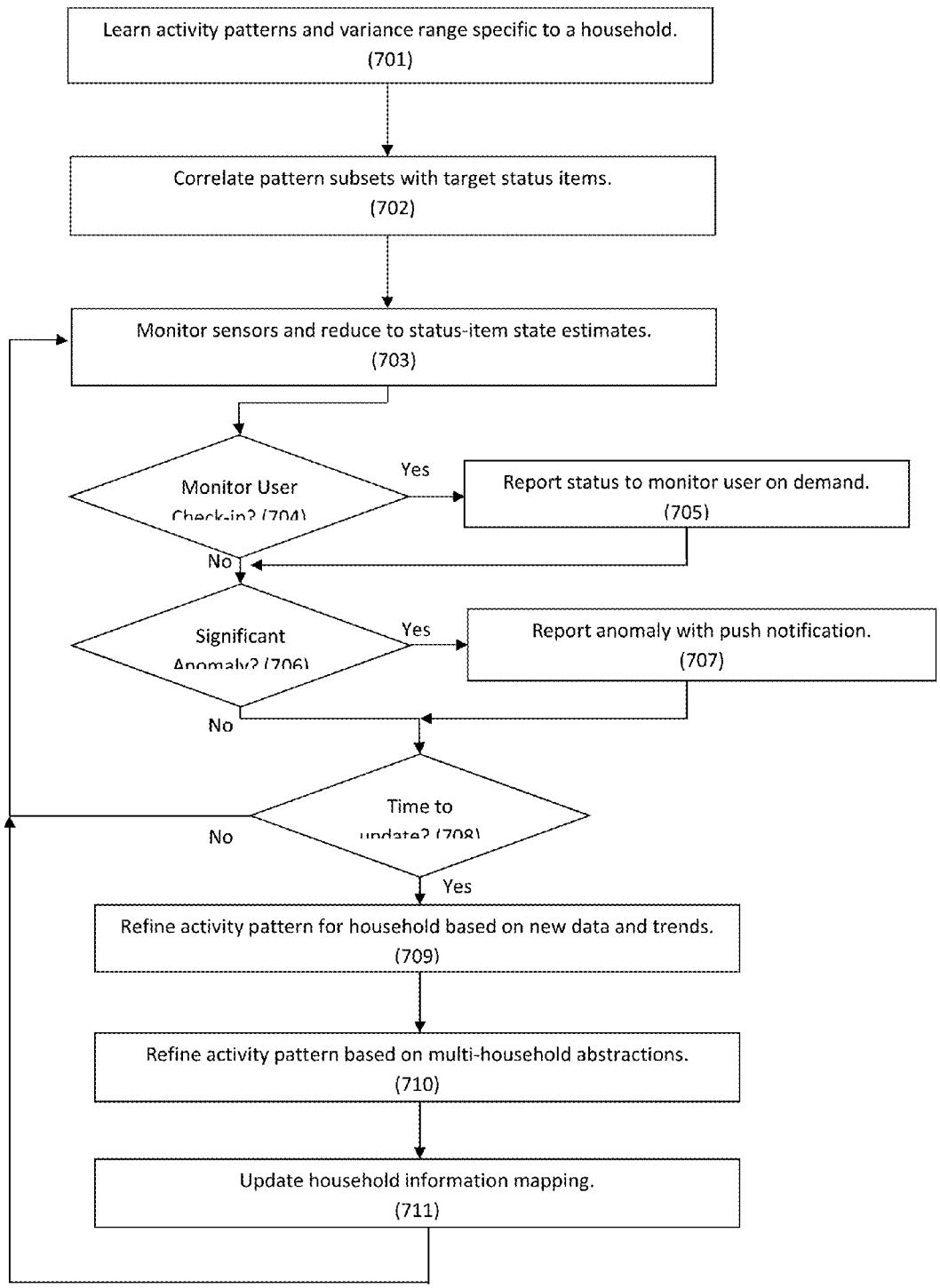
FIG. 7 is a flow diagram illustrating a flow of processes carried out during operation of the embodiment of FIG. 1 in one exemplary application.

FIG. 7 illustrates a flow of processes carried out in one example of the operational details of the system. When a monitoring system is initially deployed, the analytics component of the system is preferably activated to record and learn typical time course activity patterns of the subject(s) in the monitored environment, as indicated at process block 701. Such patterns are preferably established with respect to standardized period time references, including daily 24 hour periods with allowance for variation over the course of a given week, and in certain embodiments, with allowance for variation over longer periods such as monthly, quarterly, or seasonal variations. Calendar overlays may also consider cultural contexts such as religious events (e.g. month-long Ramadan eating changes would significantly impact both the daily pattern of eating and kitchen activity, but would likely also affect system analytics if not taken into account). An individual subject or monitoring user anticipating such pattern changes may effectuate adaptive accommodation in the system by entering known events into a system calendar. Entries such as vacation time away, medical procedures, family events, monthly meetings at the home, etc. may be made in this regard. Access to such a calendar may be shared or restricted in much the manner that access to the data stream and summary information of the subject is selectively controlled, in view of privacy and other applicable concerns.

Using domain knowledge about the setting and specific locations in which sensors are installed, coupled with general rules of typical behavior established for the subject type (e.g. elder) among other things, the system's analytics component maps sensed event/activity patterns to event types which denote certain conduct of the subject, as indicated at process block 702. For example, night time bedroom activity followed by a quiet period (little or no activity) is mapped to a "gone to bed" event. A quiet period followed by morning bedroom activity, then activity outside of the bedroom, is mapped to a "wake up event." Morning kitchen events in certain time ranges and duration are mapped to breakfast eating events. Midday kitchen events of consistent duration are mapped to a "lunch" eating event, and so forth. Other examples for various other areas within the monitored setting, and for different applications involving different types of subjects and/or setting will be apparent to those skilled in the art.

The system in the illustrated embodiment makes such inferences for: wake-up and sleep events; nap events; and, breakfast, lunch, dinner, snack/coffee consuming events. The system also makes such inferences for daily activity periods and appliance or lighting usage patterns, as learned for a particular target subject (as further exemplified in FIG. 9).

The system then enters its active monitoring mode. At block 703, sensor data streams are continuously monitored and periodically mapped to state estimates, corresponding to the event types of interest. This status information is maintained in quasi real-time and is available for a monitoring user to check on demand. In accordance with block 704, if a monitoring user checks for a status update, then the system at block 705 presents the information using, for example, one of the interfaces illustrated in FIGS. 4-6.

In accordance with block 706, if a significant deviation from one or more normal activity patterns is detected, and the system determines for the prevailing context that there is possible reason for concern, the system at block 707 pushes this information actively to the monitoring user via their preferred mode of notification. What categories are of interest and the degree of anomaly that rises to a level of significance is determined in accordance with each monitoring user's preferences and selective configuration of system settings. The level of significance pertaining to particular activities in certain embodiments, is also dependent upon the system's determination of whether deviation from a pattern is benign (e.g., increased activity due to Grandma's bridge night) or potentially of concern (e.g., increased activity remains unexplained, or occurs in association with alarming sensor events such as a smoke detector or environmental sensor indicating out of range conditions.)

At block 708 the system determines if it is appropriate to update the patterns initially established at blocks 701 and 702. In various embodiments of the system, different analytic approaches are used singularly or jointly to determine when such an update is warranted. In one example, updates may occur on a regularly scheduled basis. In another example, updates may occur when records of activity patterns indicate that the subject(s) in a setting (household) is no longer conforming to those initially established at block 701. Thus, the system progressively adapts to changing behaviors of the target subject. In a further example, updates may occur when sufficient data is gleaned from aggregate analysis of other subjects (households) to establish new generalizations appropriate for propagation to the monitoring of other individual subjects within the group. In still another example, updates may occur because changes in software or in event categories warrant such updates.

Should updates be in order, the updates generally relate to two refinement types. The first, indicated at block 709, effects a re-analysis of current data logs to update household specific (or subject and/or setting specific) patterns that were originally recorded at block 701. The second, indicated at block 710, effects refinement in the understanding and abstraction of these patterns based on other information learned in aggregate from multiple households (subjects and/or settings) of a similar category. At block 711, the affected event patterns are re-mapped to the target status event items of interest, so that the analytics component may begin reporting states and events of interest in accordance with the goals of the system.

Other examples of scenarios relevant to monitoring subjects in the particular case of elderly subjects, whose infirmities derive primarily from their advanced age, include the following:

Grandmother A has a predictable morning wake time, and consistently opens the refrigerator for milk for her coffee and cereal between 7:15 and 7:30 AM every morning for 3 months. The next morning activity is seen in the bedroom at 7 am as usual, but the hallway motion sensor does not detect activity as usual, and the refrigerator door is not opened as usual by 8 am. The analytics component of the system infers based on the combination of sensed events that Grandmother A got up, didn't feel well, and went back to bed. Depending on the system's settings configuration, this contextualized conclusion constitutes detection of Grandmother A's conduct sufficiently anomalous to trigger alert notification to one or more monitoring caregivers to check on her.

Grandfather B watches the 5 pm news every day of the week, but not on weekends. On a Tuesday early in July Grandfather B fails to watch the news, which would normally constitute an anomalous event for Tuesdays. However, the calendar overlay identifies that particular Tuesday as the $4^{th}$ of July, so the system does not immediately report the event to the monitoring caregiver (Grandfather B's son) based on known similarities of July $4^{th}$ holiday to a weekend day. However, when Grandfather B does not turn on his reading light in his family room by 8 pm, an event consistent with event patterns for both weekdays and weekends, anomalous conduct is detected and Grandfather B's caregiver is notified. The son, however, knows of Grandfather B's whereabouts (with his own family at that moment), so the alert notification is disregarded not followed up on, yet the son remains reassured that the system's analytics are operating properly.

These are but examples, and numerous other scenarios such as these are supported by the illustrated embodiment.

Suitable software and hardware measures for machine learning known in the art may be employed to carry out such automated decision making according to the particular requirements of the intended application. In a first configuration, the system provides for a plurality of predefined pattern event scenarios, and the conditions required for detection as anomalous conduct. These are preferably recorded in a set of expert system rules, and acted upon based on logic described according to the sensor inputs that have been tokenized into events of specific types. This provides a fully enabled mechanism by which to implement many of the features and goals noted herein.

However, in certain preferred embodiments of the present system and method, the discovery and processing of pattern event scenarios is substantially automated, rather than predefined by human analyst(s). In particular, as discussed with reference to FIG. 7, the system undergoes a learning phase of operation to first forms an event frequency distribution according to defined time cycles, including hours in a day, days in the week, etc. The system then tokenizes consistent patterns and associates them with a priori classes of typical events (bed times, meals, etc.), and/or subject-specific events (time-consistent room use activities or appliance-use activities). The degree of deviation or compliance with such learned schedules of events, as will be understood by those skilled in the art, may be readily determined by statistical or Bayesian estimates of likelihood and confidence in the appropriate context. Information both learned in the context of a particular subject's household activities and directly established by human analysts may be combined through joint and conditional probabilities to provide maximum likelihood estimations of the target subject's state of well-being.

Figure 9:
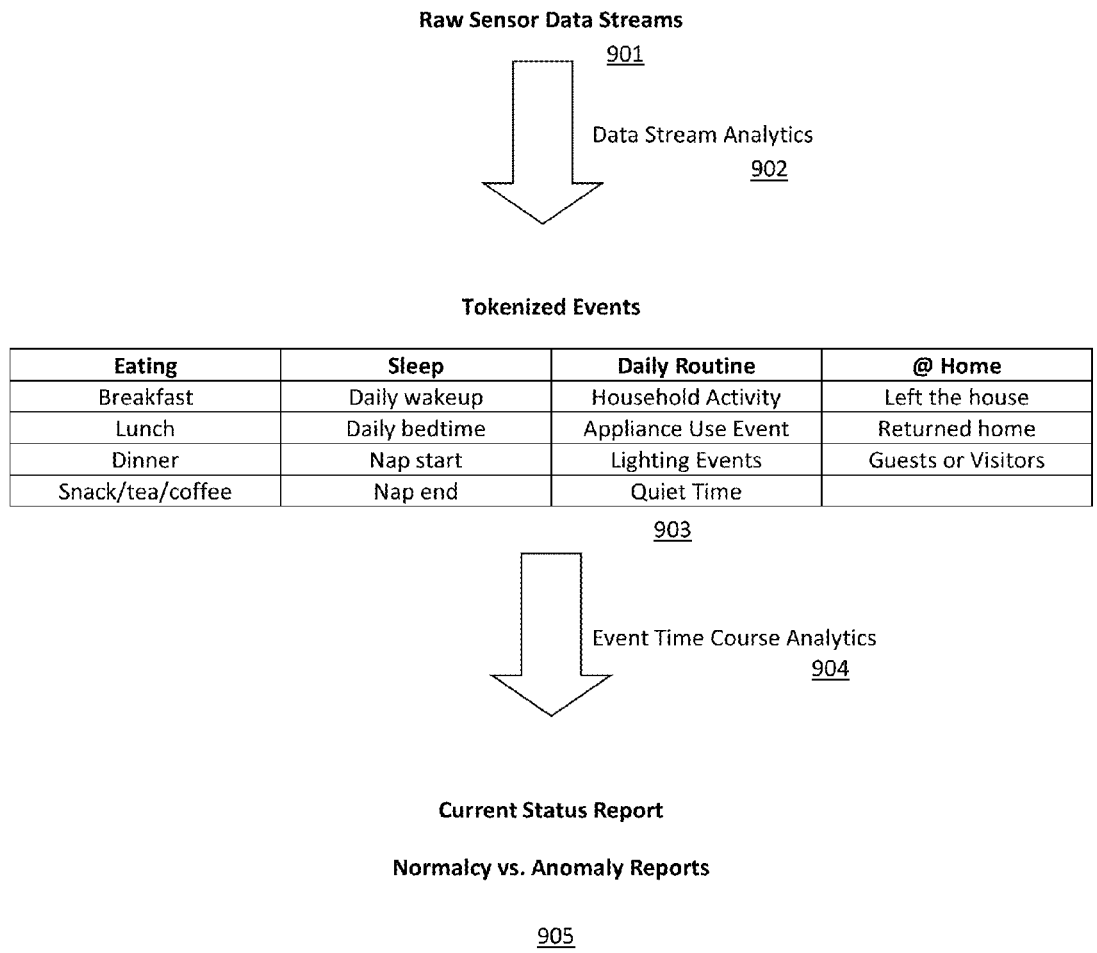

FIG. 9 schematically illustrates a general approach carried out in accordance with the illustrated embodiment for reducing the sensor data acquired by the system. Raw sensor data streams 901 are mapped by data stream analytics portion 902 to certain tokenized events 903. The examples of tokenized events shown are provided for purposes of illustration with reference to the illustrated embodiment and sample application, and obviously without limitation of other embodiments and applications thereto. These event courses are analyzed with respect to their expected time courses 801, to determine (a) the current activity state of the monitored individual and (b) whether that activity state is nominal or anomalous.

Figure 8:
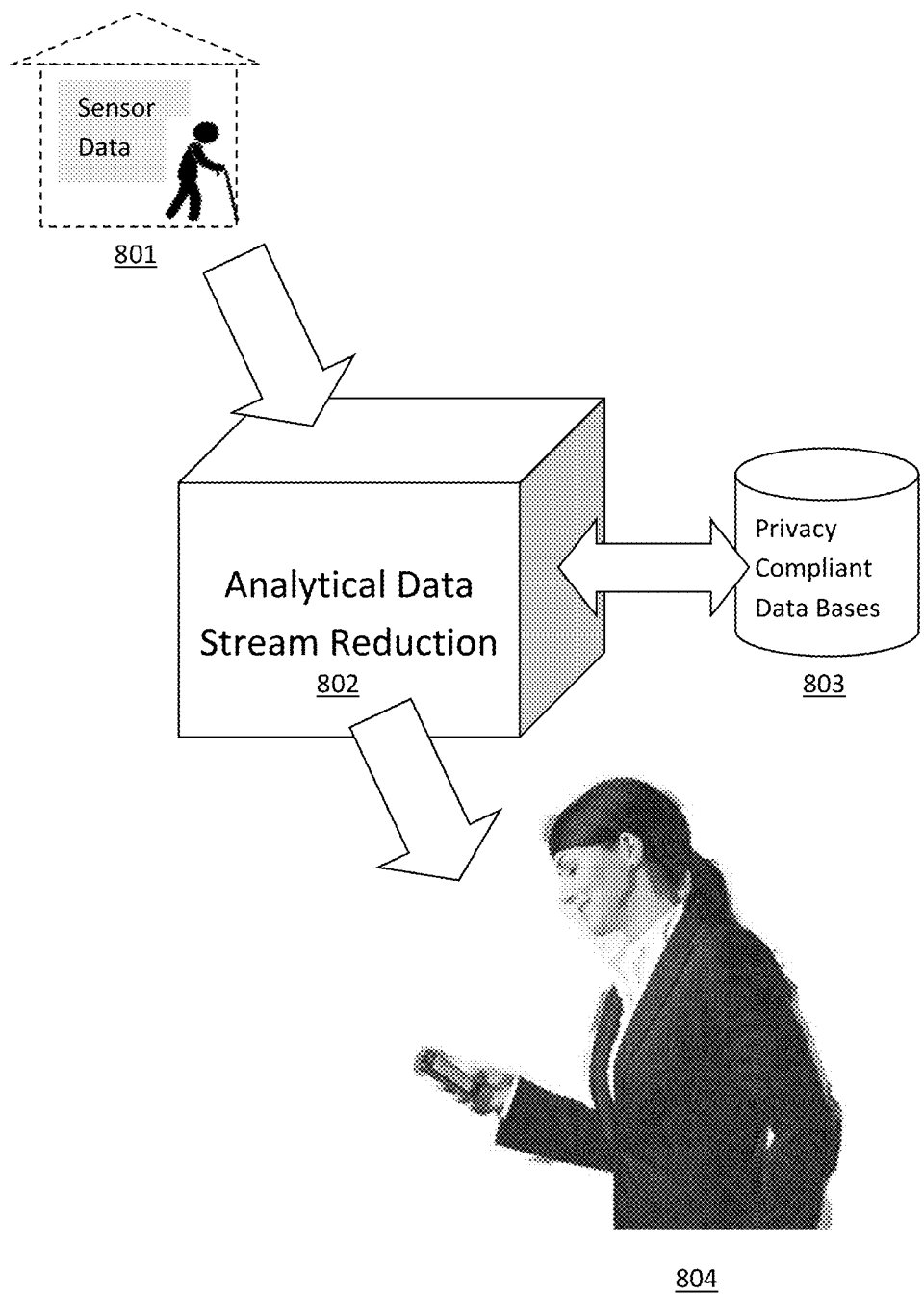
FIG. 8 is schematic diagram illustrating a flow of data as it is reduced from a complicated, as-available sensor data stream to a clear, concise, privacy compliant presentation for a monitoring user during operation of the embodiment of FIG. 1 in one exemplary application; and, FIG. 9 is schematic diagram generally illustrating a reduction of sensor data streams from raw sensor data, to tokenized events of interest, then to an at-a-glance presentation for a monitoring user during operation of the embodiment of FIG. 1 in one exemplary application.

The event data-activity report mapping measures illustrated in FIG. 9 support the general monitoring operation schematically illustrated in FIG. 8. As shown in FIG. 8, the complex streams of sensor data are collected using available sensors in the quasi-controlled setting 801 in spaces and equipment surrounding a target subject. The collected data is reduced through the analytical processing portion 802 to produce at-a-glance, quickly understandable reports of status information about the target subject's activity, and made available to a monitoring user 804 anywhere in the world through a linked personal communication device. The monitoring user is thereby presented with quick, easily understood, and to the point information on the subject's current state of well-being. The target subject enjoys maximum privacy with respect to the moment to moment details of their activities, as they and their immediate movements are not directly monitored. Moreover, the target subject need not take active steps to facilitate the monitoring, even while sufficiently complete presentation of pertinent well-being information is made available to a monitoring user through the simple touch of an icon.

Upon reviewing the novel combinations of elements disclosed in the specification and figures and the teachings herein, it will be clear to those skilled in the art that there are many ways in which the subject system and method may be implemented and applied. The above description relates to the preferred modes and example embodiments of the invention. The descriptions above are intended to illustrate possible implementations of the present invention and are not restrictive. The inventors contemplate variations and additional features and functions within the skill of the art, including advances in operational technology. Various modifications other than those discussed above may be resorted to without departing from the spirit or scope of the invention. Variations, modifications and alternatives will become apparent to the skilled artisan upon review of this disclosure. For example, equivalent elements may be substituted for those specifically shown and described. Certain features may be used independently of other features, various methods independently described may be combined, and in certain cases, particular locations of elements may be reversed or interposed, all without departing from the spirit or scope of the invention as defined in the appended claims.

What is claimed is:

1. A system for indirect event-based monitoring of a subject for well-being within a predefined unattended setting, comprising:
    a plurality of sensors disposed strategically throughout the predefined setting for respectively sensing disparate events occurring within the predefined setting;
    an analytics processing portion coupled to said sensors, said analytics processing portion being programmably configured for execution to:
        collectively acquire sensing data for the disparate events respectively from a selected combination of said sensors without video surveillance, wherein:
            each of said sensors in the selected combination transduces a physically measurable condition;
            at least one of said sensors in the selected combination indirectly detects activity of the subject, and is selected from the group consisting of: light sensors, energy management sensors, power use sensors, entertainment device use sensors, contact sensors, drawer opening/closing sensors, work space sensors, lighting actuation sensors, home automation sensors, glass breakage sensors, water flow sensors, moisture sensors, and pressure sensors; and,
            each of said sensors in the selected combination is being situated apart from the subject and independent of subject movement;
        map a plurality of sensed data points from the acquired sensing data of the selected combination of said sensors to at least one conduct adaptively inferred for the subject from the corresponding disparate events, and based in part on the activity indirectly detected by the at least one sensor, the sensed data points being mapped according to a set of pre-established reference event patterns;
        screen each adaptively inferred conduct for excessive aberration with reference to said pre-established reference event patterns; and,
        actuate generation of a graphic user interface displaying at least one reporting page, said reporting page containing for each adaptively inferred conduct graphic indicia determined responsive to the screening thereof; and,
    at least one monitoring device coupled to said analytics processing portion by a wireless communications link, said monitoring device configured to render said graphic user interface for a remotely disposed monitoring user responsive to said analytics processing portion.

2. The system as recited in claim 1, wherein said analytics processing portion actuates a learning phase of operation to automatically generate at least one of said pre-established reference event patterns.

3. The system as recited in claim 2, wherein said analytics processing portion in the learning phase:
    generates a frequency distribution of sensed events within the setting according to predefined time cycles;
    adaptively learns from the frequency distribution at least one tokenized consistent pattern of sensed events; and,
    associates with the tokenized consistent pattern at least one class of predefined behavioral activities.

4. The system as recited in claim 1, further comprising a conglomerate database coupled to said analytics processing portion, said conglomerate database storing sensing data collectively acquired from sensors disposed within said predefined settings of a plurality of different subjects.

5. The system as recited in claim 4, wherein said analytics processing portion executing aggregate analysis on the sensing data from said conglomerate database, said analytics processing portion executing to:
    remove personally identifiable information and thereby anonymize the sensing data acquired from the different subjects;
    carry out longitudinally analytics over data for selected groupings of the different subjects to generate event patterns and corresponding behavioral activities therefrom; and,
    selectively including the generated event patterns within the set of said pre-established reference event patterns.

6. The system as recited in claim 1, wherein said analytics processing portion selectively reduces the sensing data acquired from said sensors to visually display in said graphic user interface reporting page a collective summary thereof according to each conduct adaptively inferred for the subject.

7. The system as recited in claim 6, wherein said graphic user interface includes a plurality of reporting page levels, said reporting page at each successive level including a more detailed presentation of well-being data presented at a portion of said reporting page, said reporting page at an initial level including a monitoring user-actuable log-in icon.

8. The system as recited in claim 7, wherein said reporting page at the initial level displaying for each adaptively inferred conduct one of two alternative graphic indicia to alternatively denote detection of nominal or anomalous aberration in the subject's conduct.

9. A system for indirect event-based monitoring of an infirm subject for well-being within a predefined unattended setting, comprising:
    a plurality of sensors disposed strategically throughout the predefined setting for respectively sensing disparate events occurring within the predefined setting;
    an analytics processing portion coupled to said sensors, said analytics processing portion being programmably configured for execution to:
        collectively acquire sensing data for the disparate events respectively from a selected combination of said sensors without video surveillance, wherein:
            each of said sensors in the selected combination transduces a physically measurable condition;
            at least one of said sensors in the selected combination indirectly detects activity of the subject, and is selected from the group consisting of: light sensors, energy management sensors, power use sensors, entertainment device use sensors, contact sensors, drawer opening/closing sensors, work space sensors, lighting actuation sensors, home automation sensors, glass breakage sensors, water flow sensors, moisture sensors, and pressure sensors; and,
            each of said sensors in the selected combination is situated apart from the subject and independent of subject movement;
        periodically map a plurality of sensed data points from the acquired sensing data of the selected combination of said sensors to at least one conduct adaptively inferred for the subject from the corresponding disparate events, and based in part on the activity indirectly detected by the at least one sensor, the sensed data points being mapped according to a set of pre-established reference event patterns, the acquired sensing data being reduced by the mapping;

determine a degree of anomaly for each adaptively inferred conduct with respect to said pre-established reference event patterns therein; and, actuate generation of a graphic user interface displaying at least one reporting page presenting a collective summary of the acquired sensing data relating to each conduct adaptively inferred for the subject, said reporting page containing for each adaptively inferred conduct graphic indicia corresponding to said degree of anomaly determined therefor; and, at least one remote monitoring device coupled to said analytics processing portion by a wireless communications link, said monitoring device configured to render said graphic user interface for a remotely disposed monitoring user responsive to said analytics processing portion.

10. The system as recited in claim 9, wherein said analytics processing portion actuates a learning phase of operation to automatically generate at least one of said pre-established reference event patterns, said analytics processing portion in the learning phase:

generating a frequency distribution of sensed events within the setting according to predefined time cycles;

adaptively learning from the frequency distribution at least one tokenized consistent pattern of sensed events; and, associating with the tokenized consistent pattern at least one class of predefined behavioral activities.

11. The system as recited in claim 10, wherein said graphic user interface includes a plurality of reporting page levels, said reporting page at each successive level including a more detailed presentation of well-being data presented at a portion of said reporting page, said reporting page at an initial level including a monitoring user-actuable log-in icon.

12. The system as recited in claim 11, wherein said reporting page at the initial level displaying for each adaptively inferred conduct one of two alternative graphic indicia to alternatively denote detection of nominal or anomalous aberration in the subject's conduct.

13. The system as recited in claim 9, further comprising a conglomerate database coupled to said analytics processing portion, said conglomerate database storing sensing data collectively acquired from sensors disposed within said predefined settings of a plurality of different subjects.

14. The system as recited in claim 13, wherein said analytics processing portion executing aggregate analysis on the sensing data from said conglomerate database, said analytics processing portion executing to:

remove personally identifiable information and thereby anonymize the sensing data acquired from the different subjects;

carry out longitudinally analytics over data for selected groupings of the different subjects to generate event patterns and corresponding behavioral activities therefrom; and, selectively including the generated event patterns within the set of said pre-established reference event patterns.

15. A method for indirect event-based monitoring of a subject for well-being within a predefined unattended setting, comprising:

selectively installing a plurality of sensors strategically throughout the predefined setting to respectively sense disparate events occurring within the predefined setting responsive to daily activity of the subject;

executing a programmably configured analytics processing portion coupled to said sensors to:

collectively acquire sensing data for the disparate events respectively from a selected combination of said sensors without video surveillance, wherein:

each of said sensors in the selected combination transduces a physically measurable condition;

at least one of said sensors in the selected combination indirectly detects activity of the subject, and is selected from the group consisting of: light sensors, energy management sensors, power use sensors, entertainment device use sensors, contact sensors, drawer opening/closing sensors, work space sensors, lighting actuation sensors, home automation sensors, glass breakage sensors, water flow sensors, moisture sensors, and pressure sensors; and, each of said sensors in the selected combination is situated apart from the subject and independent of subject movement;

map a plurality of sensed data points from the acquired sensing data of the selected combination of said sensors to at least one conduct adaptively inferred for the subject from the corresponding disparate events, and based in part on the activity indirectly detected by the at least one sensor, the sensed data points being mapped according to a set of pre-established reference event patterns;

screen each adaptively inferred conduct for excessive aberration with reference to said pre-established reference event patterns; and, actuate generation of a graphic user interface displaying at least one reporting page, said reporting page containing for each adaptively inferred conduct graphic indicia determined responsive to the screening thereof;

establishing at least one monitoring device coupled to said analytics processing portion by a wireless communications link; and, configuring said monitoring device for actuation responsive to said analytics processing portion to visually render said graphic user interface for a remotely disposed monitoring user.

16. The method as recited in claim 15, wherein said analytics processing portion is actuated to execute a learning phase of operation for automatically generating at least one of said pre-established reference event patterns, said learning phase including:

generating a frequency distribution of sensed events within the setting according to predefined time cycles;

adaptively machine learning from the frequency distribution at least one tokenized consistent pattern of sensed events; and, associating with the tokenized consistent pattern at least one class of predefined behavioral activities.

17. The method as recited in claim 15, wherein:

the sensing data acquired from said sensors is selectively reduced to visually display in said graphic user interface reporting page a collective summary thereof according to each conduct adaptively inferred for the subject;

a plurality of reporting page levels are established for said graphic user interface, said reporting page at each successive level including a more detailed presentation of well-being data presented at a portion of said reporting page, said reporting page at an initial level including a monitoring user-actuable log-in icon; and, displaying with each said adaptively inferred conduct in said reporting page at the initial level one of two alternative graphic indicia to alternatively denote detection of nominal or anomalous aberration in the subject's conduct.

\* \* \* \* \*